(12) United States Patent
Reeser

(10) Patent No.: US 8,663,244 B2
(45) Date of Patent: Mar. 4, 2014

(54) SURGICAL TACK AND TACK DRIVE APPARATUS

(75) Inventor: Steven M. Reeser, Jacksonville, FL (US)

(73) Assignee: Laprotx LLC, Jacksonville, FL (US)

( * ) Notice: Subject to any disclaimer, the term of this patent is extended or adjusted under 35 U.S.C. 154(b) by 0 days.

(21) Appl. No.: 13/601,026

(22) Filed: Aug. 31, 2012

(65) Prior Publication Data

US 2013/0012961 A1 Jan. 10, 2013

Related U.S. Application Data

(62) Division of application No. 12/844,260, filed on Jul. 27, 2010, now abandoned.

(51) Int. Cl.
*A61B 17/10* (2006.01)
(52) U.S. Cl.
USPC ........................................ 606/139; 227/175.1
(58) Field of Classification Search
USPC ........... 606/139, 142, 143, 213, 219, 220, 75, 606/104; 227/175.1, 176.1, 177.1, 178.1, 227/179.1, 181.1
See application file for complete search history.

(56) References Cited

U.S. PATENT DOCUMENTS

| | | | |
|---|---|---|---|
| 1,100,252 A | 6/1914 | O'Neill | 411/456 |
| RE27,725 E | 8/1973 | Brumlik | 24/447 |
| 4,612,933 A | 9/1986 | Brinkerhoff et al. | |
| 4,976,715 A | 12/1990 | Bays et al. | 606/77 |
| 5,084,057 A | 1/1992 | Green et al. | |
| 5,333,624 A | 8/1994 | Tovey | |
| 5,557,898 A | 9/1996 | Dixon | 52/410 |
| 5,728,116 A | 3/1998 | Rosenman | |
| 6,099,552 A | 8/2000 | Adams | 606/220 |
| 6,346,109 B1 | 2/2002 | Fucci et al. | 606/104 |
| 6,447,524 B1 | 9/2002 | Knodel et al. | |
| 7,815,652 B2 | 10/2010 | Messerly et al. | |

(Continued)

FOREIGN PATENT DOCUMENTS

WO WO 2007/097994 A2 8/2007

OTHER PUBLICATIONS

International Search Report and the Written Opinion of the International Searching Authority for PCT/US2011/044927; mailed Dec. 1, 2011; 11 pages.

*Primary Examiner* — Dianne Dornbusch
*Assistant Examiner* — Robert Lynch
(74) *Attorney, Agent, or Firm* — Pandiscio & Pandiscio

(57) ABSTRACT

An applicator for applying a barbed fastener to a body tissue-is provided. The applicator comprises an elongated tubular portion having a longitudinal axis extending from a proximal end to a distal end and having a tube interior sized and configured for receiving the barbed fastener. An elongate driver is disposed at least partially inside the tube interior, the driver having a driver engaging portion at its distal end. The driver engaging portion is adapted to engage the barbed fastener in a firing position adjacent the distal end of the elongated tubular portion. The applicator also comprises; a driver actuator assembly adjacent the driver at its proximal end, the driver actuator assembly being adapted for selectively imparting an impulse force to the driver. The driver is configured for transmitting the impulse force to the barbed fastener.

11 Claims, 14 Drawing Sheets

(56) References Cited

U.S. PATENT DOCUMENTS

| | | |
|---|---|---|
| 7,905,893 B2 | 3/2011 | Kuhns et al. |
| 2002/0068947 A1 | 6/2002 | Kuhns et al. |
| 2002/0087170 A1 | 7/2002 | Kuhns et al. |
| 2004/0161319 A1 | 8/2004 | O'Banion et al. ............ 411/456 |
| 2005/0240222 A1 | 10/2005 | Shipp |
| 2006/0129154 A1 | 6/2006 | Shipp |
| 2010/0292710 A1 | 11/2010 | Daniel et al. |
| 2010/0292713 A1* | 11/2010 | Cohn et al. .................... 606/143 |

* cited by examiner

SURGICAL TACK AND TACK DRIVE APPARATUS

CROSS-REFERENCE TO RELATED APPLICATION

This application is a division of U.S. Application No. 12/844,260, filed Jul. 27, 2010 now abandoned.

FIELD OF THE ART

The present invention relates generally to surgical fasteners and drive apparatus for use with surgical fasteners. More specifically, the present invention relates to soft tissue surgical tacks and a tack drive system for the fixation of hernia mesh.

DESCRIPTION OF RELATED ART

Fasteners are used in various surgical procedures to secure tissue and objects to tissue. One such surgical procedure is the repair of a hernia. A common solution in hernia repair is to attach a mesh patch over the defect so that bowel and other abdominal tissue are blocked from forming an external bulge that is typical of abdominal hernias.

At present, there are a variety of devices and fasteners available to attach the mesh patch to the inguinal floor or abdominal wall. Such devices and fasteners include sutures, surgical staples, and tacks. The role of the devices and fasteners is to keep the mesh in proper position until tissue in-growth is adequate to hold the mesh in place under various internal and external conditions.

A hernia repair surgery can be performed either through the traditional open procedure or through the current trend of less invasive procedures such as laparoscopic procedures. Certain previously used devices and fasteners are better suited for open procedures while other devices and fasteners are better suited for laparoscopic procedures.

SUMMARY

In view of the foregoing, there exists a need for a hernia mesh fastener that is simple to deploy, securely fastens to bodily tissue, and can be absorbed by the body after a period of time when the tissue in-growth to the mesh obviates the need for a fastener. A need also exists for a simple inexpensive fastener drive apparatus that is easy to handle and use by a surgeon and is adaptable for use in both open and laparoscopic procedures. Accordingly, various embodiments disclosed herein provide a fastener, a drive apparatus, and a method for using the drive apparatus to apply a fastener It is therefore a feature of an embodiment to provide a fastener for attaching to a body tissue, having a longitudinal direction, a proximal end, and a distal end. The fastener comprises a head portion disposed near the proximal end of the fastener and having a proximal surface, a distal surface, and a passage that extends through the head portion from the proximal surface to the distal surface. The fastener further comprises a body portion extending from the distal surface of the head portion in the longitudinal direction. The fastener further comprises an anchoring element extending from the body portion, and including at least one barb that is at least partially disposed adjacent the distal end of the fastener.

It is another feature of an embodiment to provide an applicator for applying a barbed fastener to a body tissue, the applicator comprising an elongated tubular portion having a longitudinal axis extending from a proximal end to a distal end and having a tube interior accessible by proximal and distal tube openings. The tube interior is sized and configured for receiving the barbed fastener. The applicator further comprises an indexer disposed at least partially inside the tube interior. The indexer has an elongated indexer body member and a fastener engaging portion adapted to engage the barbed fastener and move the barbed fastener from an initial fastener position in the tube interior to a firing position as the indexer moves from a first longitudinal position to a second, more distal longitudinal position. The applicator also comprises a driver disposed at least partially inside the tube interior. The driver has a driver engaging portion at its distal end. The driver engaging portion is adapted to engage the barbed fastener in the firing position and selectively apply an ejection force to the barbed fastener, thereby ejecting the barbed fastener from the tube interior through the distal opening.

It is another feature of an embodiment to provide a method a method of applying a fastener to a pre-determined target insertion point on a body tissue. The method comprises providing a fastener having a head portion having a passage formed therethrough, an anchoring element configured for engaging the body tissue, and a body portion extending distally from the head portion to connect the anchoring element thereto. The method further comprises providing a fastener applicator comprising an elongated tubular portion having a longitudinal axis extending from a proximal end to a distal end and having a tube interior accessible by proximal and distal tube openings, an indexer disposed at least partially inside the tube interior, the indexer being adapted to selectively move the fastener from an initial position to a firing position adjacent the distal tube opening, and a driver disposed at least partially inside the tube interior, the driver being adapted to engage the fastener in the firing position and selectively apply an ejection force to the fastener. The method still further comprises placing the fastener in the initial position within the tube interior and causing the indexer to selectively move the fastener from the initial position to the firing position. The method also comprises positioning the distal opening of the tube assembly adjacent the target insertion point and causing the driver to apply the ejection force to the fastener, thereby ejecting the fastener through the distal opening and into the body tissue at the target insertion point.

These and other objects, features, and advantages of the present invention will appear more fully from the following description of the exemplary embodiments, taken in conjunction with the accompanying drawings.

DETAILED DESCRIPTION OF THE EMBODIMENTS

Figure 1:
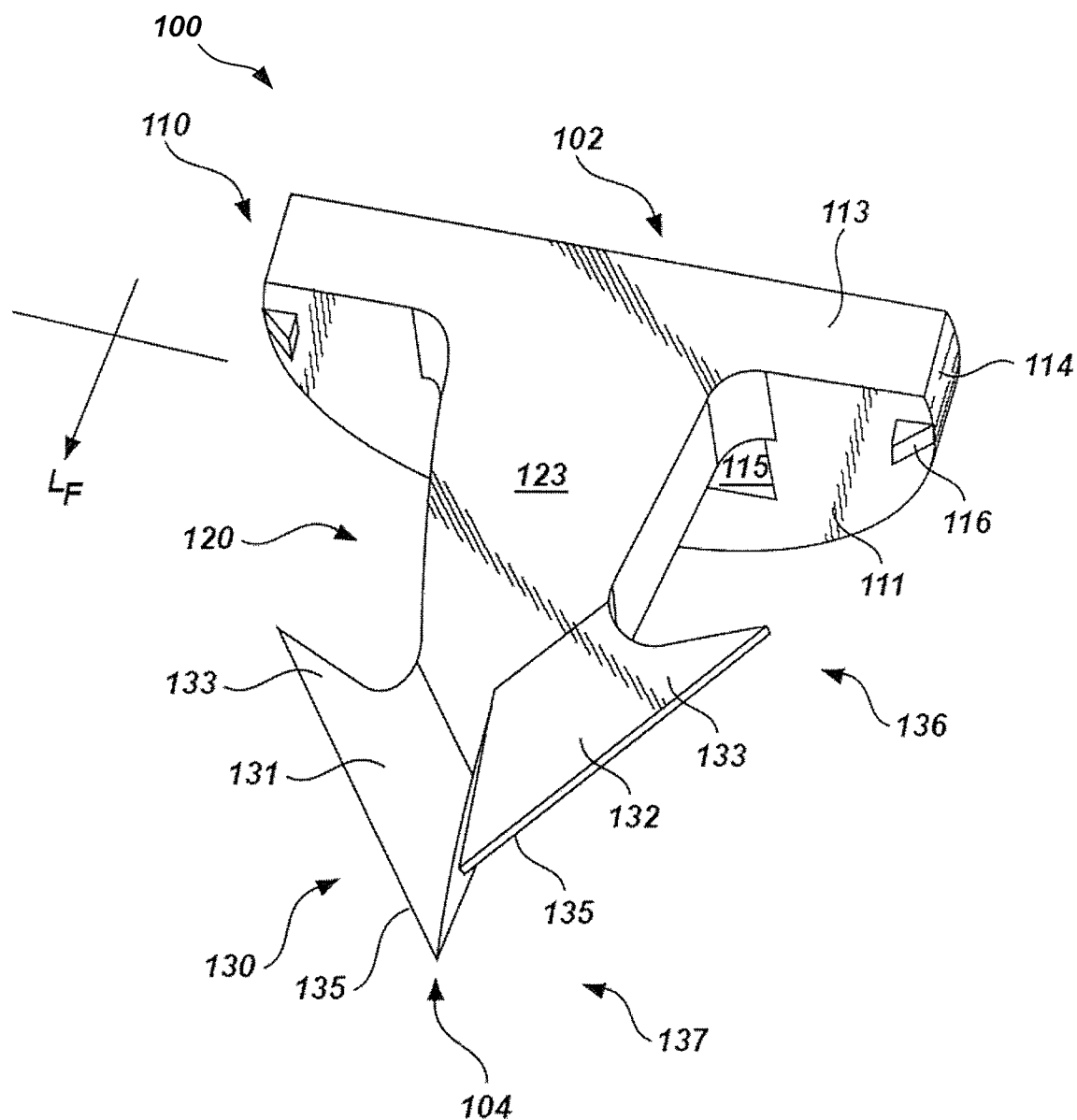
FIG. 1 is a perspective view of a fastener in accordance with an exemplary embodiment.
Figure 2:
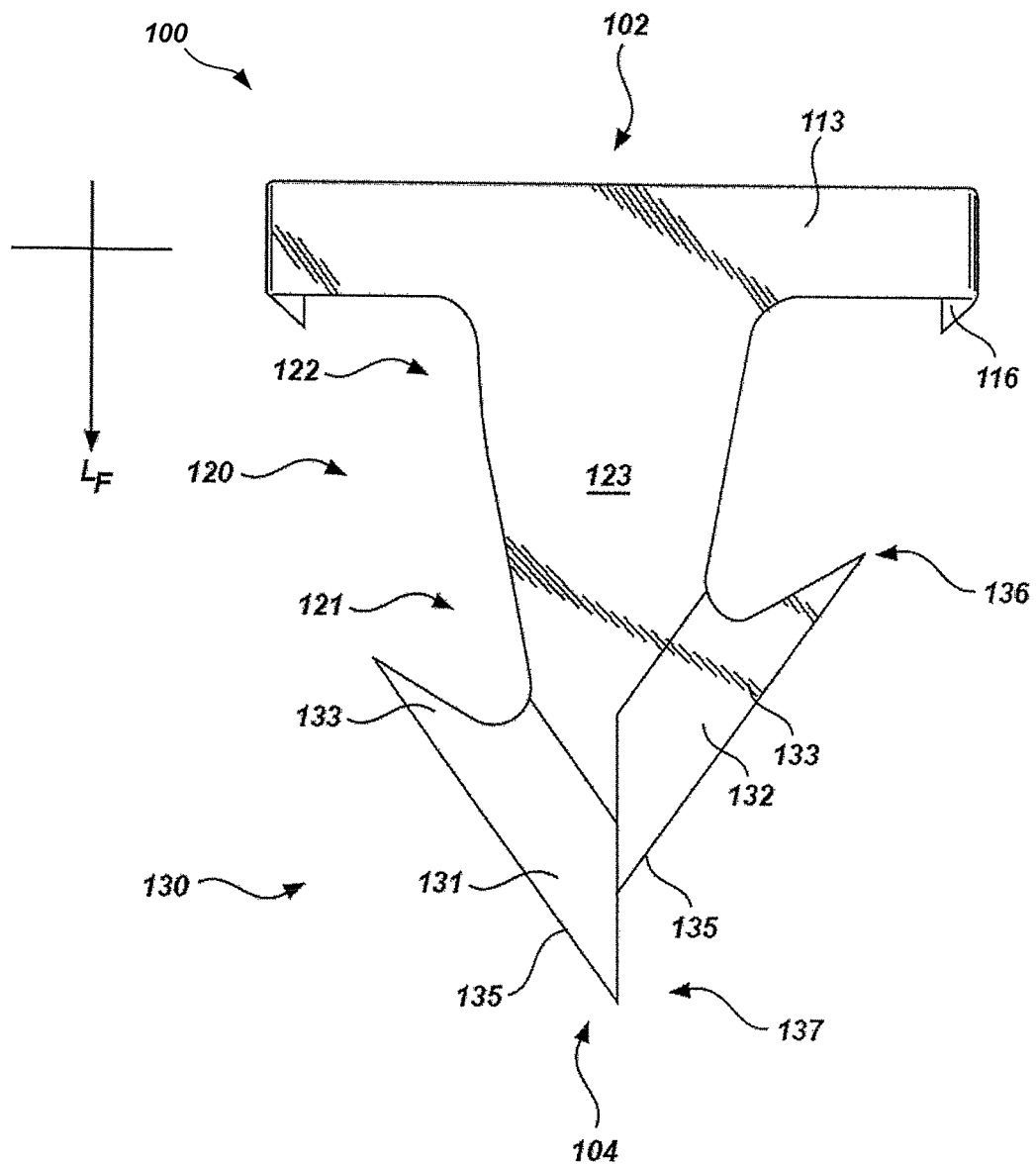
FIG. 2 is a top view of a fastener in accordance with an exemplary embodiment.
Figure 3:
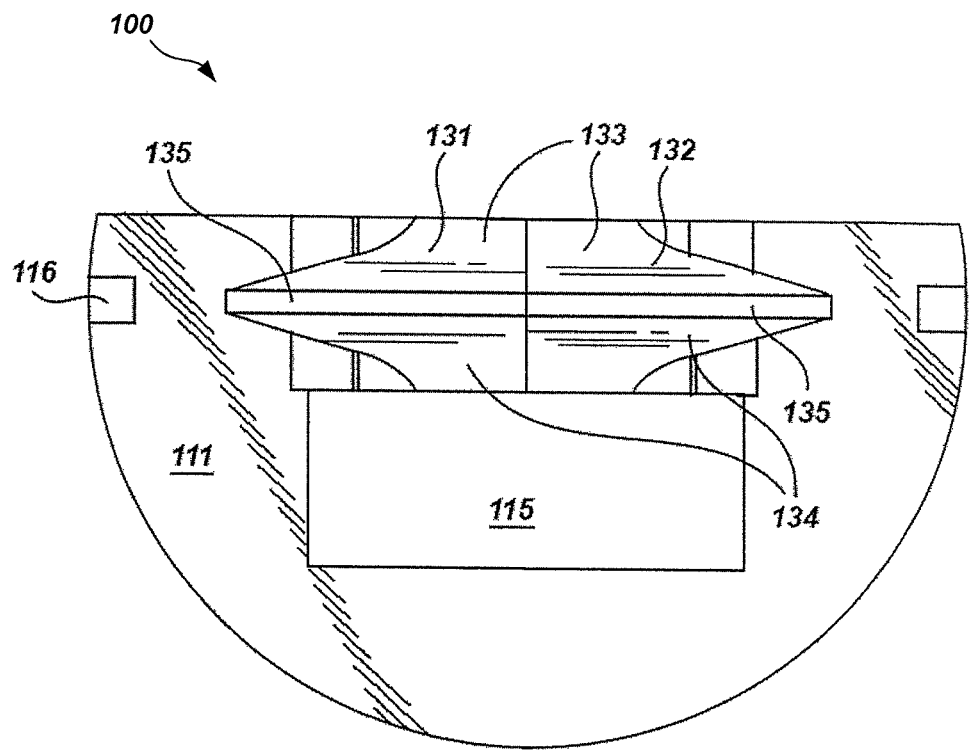
FIG. 3 is a front view of a fastener in accordance with an exemplary embodiment.
Figure 4:
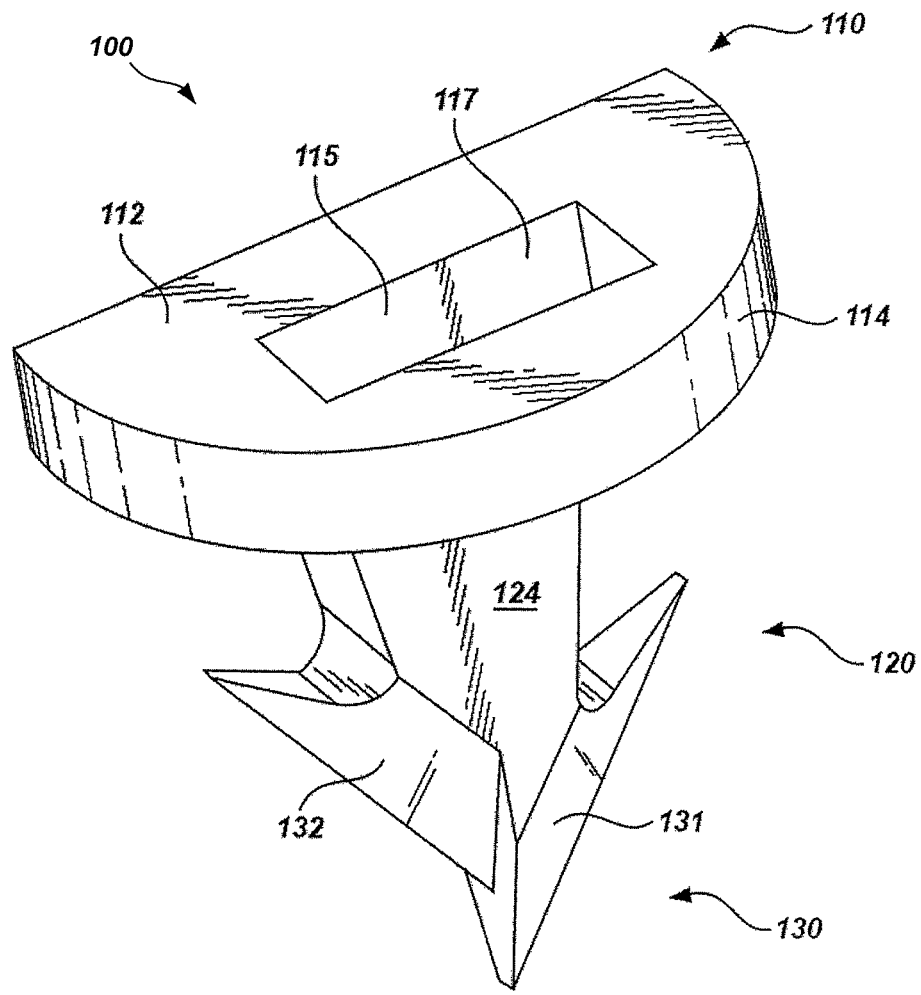
FIG. 4 is a perspective view of a fastener in accordance with an exemplary embodiment.

Hereinafter, aspects of methods and apparatuses in accordance with various exemplary embodiments will be described. As used herein, any term in the singular may be interpreted to be in the plural, and alternatively, any term in the plural may be interpreted to be in the singular.

As used herein, the term "proximal" refers to the portion of a fastener or fastener drive apparatus closest to the user (i.e., the person inserting the fastener), while the term "distal" refers to the portion of a fastener or fastener drive apparatus furthest from the user.

Exemplary embodiments include a fastener and fastener drive apparatus for use in surgical procedures. By way of example, the embodiments are illustrated and described in reference to devices and methods used in conjunction with a hernia repair procedure using a mesh patch. Thus, in the exemplary embodiments, the fasteners may be referred to as a hernia mesh tack and the drive apparatus may be referred to as a tack drive apparatus. However, it is appreciated that the exemplary embodiments are applicable to various other surgical procedures that require the use of a fastener and a fastener drive apparatus.

The fasteners of the exemplary embodiments are configured to secure body tissue to body tissue, or to secure another material, such as a mesh, to body tissue. For example, a fastener of the exemplary embodiments may be used as a hernia tack that secures a mesh structure to body tissue in a hernia repair procedure. In the exemplary embodiments, the hernia tack is of the axial insertion or "push" type variety and is configured for insertion upon application of a rapid axial insertion impulse, as compared to a steady, drawn out insertion force. The hernia tack of the exemplary embodiments includes barbs that enable easy penetration of the tissue with minimal tissue cutting. The fasteners of the exemplary embodiments can be used in conjunction with a drive apparatus that is configured to position a fastener for insertion, and to apply a rapid insertion impulse to the fastener to permanently insert the fastener into a body tissue. Various exemplary embodiments of such fasteners and drive apparatuses are described in more detail below.

Referring now to FIGS. 1-4, in which like reference numerals identify similar or identical elements, the details of an exemplary embodiment of a fastener 100 are described in greater detail. Generally, the fastener 100 has a longitudinal direction $L_F$, as indicated by the arrow in FIG. 1. Along the longitudinal direction, the fastener 100 has a distal end 104, and a proximal end 102. In the exemplary embodiments, the distal end 104 of the fastener 100 generally is the portion of the fastener 100 that is first inserted through the body tissue. In the embodiments, the fastener 100 includes an anchoring element 130 located near the distal end 104 of the fastener 100, a head portion 110 located near the proximal end 102 of the fastener 100, and a body portion 120 located intermediate the two ends 102, 104, connecting the anchoring element 130 and the head portion 110.

In the exemplary embodiments, the head portion 110 of the fastener 100, can be configured to engage with a body tissue, or other material, such as a mesh, to hold the tissue or material in place against a body tissue. As illustrated in FIGS. 1-4, in the exemplary embodiments, the outer surface of head portion 110 of the fastener 100 can include a distal head face 111, a proximal head face 112, an upper head face 113, and a lower head face 114. Each of the faces 111, 112, 113, 114, can be flat or substantially flat surfaces, or they can be arcuate to provide a concave or convex surface. For example, in the exemplary embodiment illustrated in FIGS. 1-4, upper head face 113 is a flat surface, and lower head face 114 is generally an arcuate surface with a convex shape, such as one formed by a smooth arcuate surface, or a series of adjoining arcuate or flat facets. In exemplary embodiments, the arc defined by the lower head face 114 can extend at least about 180 degrees and less than 360 degrees. In the embodiment illustrated in FIGS. 1-4, the arcuate lower head face 114 provides a 180 degree arc that connects one transverse edge of the upper head face 113 to the other transverse edge of the upper head face 113. It is appreciated that any or all of the faces 111, 112, 113, 114, can be configured to have any desired shape In various embodiments, the head portion 110 may have a passage 115 that extends through the head portion 110 from the proximal head face 112 to the distal head face 111. The passage 115 is configured to enable the fastener 100 to slide along the drive sequencing indexer mechanism, as will be discussed in more detail later. In exemplary embodiments, the passage 115 may be shaped in such a way as to compliment the shape of the indexer. For example, the passage 115 may be in the form of a bore or a channel that at least partially surrounds the indexer, enabling the fastener 100 to slide along the indexer. For example, in embodiments in which the indexer has a rectangular cross-sectional shape, the passage 115 may have a corresponding rectangular shaped bore. In other exemplary embodiments, the passage 115 may be formed as a channel rather than a closed passage, so that it surrounds only a portion of the indexer. It will be understood that the passage 115 may be configured in other suitable forms and shapes suitable for adapting the fastener to slide along an indexer. The head portion 110 also may be configured to facilitate deployment from an applicator.

In various exemplary embodiments, the head portion 110 may include one or more anchoring devices such as anchor tabs 116 extending from the distal head face 111. The anchor tabs 116 may be configured to assist in anchoring the mesh or other material in place when the fastener 100 is inserted. The anchor tabs 116 may provide an attachment that secures more readily to large-holed mesh. For example, during hernia surgery, the anchor tabs 116 may engage the hernia mesh strand to provide a more secure bond between the mesh and the tissue. The anchor tabs 116 may have any shape that would enable the tabs 116 to anchor the mesh. For example, in embodiments such as those illustrated in FIGS. 1-4, the anchor tabs 116 may have a triangular shape. It will be understood that the anchor tabs 116 may have many alternative shapes.

In various exemplary embodiments, the body portion 120 of fastener 100 extends distally from the head portion 110, and has a proximal body end 122 joined with the distal head face 111, and a distal body end 121. In exemplary embodiments, the body portion 120 and the head portion 110 may be integrally formed to form a single unit. However, it will be understood that the body portion 120 and head portion 110 may be separately formed, and joined together to form the fastener 100. The body portion 120 additionally may have an upper body face 123 and a lower body face 124. In exemplary embodiments, the upper body face 123 and the lower body face 124 may have flat or substantially flat surfaces, or surfaces that have a partial curve. In some embodiments, the upper body face 123 may be coplanar with the upper head face 113. In some embodiments, the lower body face 124 may be coplanar with the upper passage surface 117.

In exemplary embodiments, the distal body end 121 may have one or more anchoring elements 130. The anchoring element 130 and body portion 120 may be integrally formed, or may be separately formed and operably joined together. In the embodiment illustrated in FIGS. 1-4, the anchoring element 130 has a pair of barbs 131, 132. Barbs 131,132 may have a proximal anchor point 136 that has a width (measured at its widest point) that is wider than the distal edge 137, which prevents expulsion or removal of the fastener 100 from the body tissue once the fastener 100 is applied. The barbs 131,132 also may have upper facets 133 and lower facets 134 that taper to an angled leading edge 135. The leading edge 135 is configured to have a cutting portion and a stretching portion. When the fastener 100 is inserted, the width of the incision is only as wide as the effective diameter from the proximal ends of the cutting portions of the two barbs 131, 132. The stretching portion serves to widen the incision to admit the tack without further tissue cutting. When the barbs 131, 132 are fully inserted into the tissue the stretched incision tends to close back up, thereby improving the security of the tissue attachment to the inserted fastener 100.

In some embodiments, the first barb 131 is longitudinally offset from the second barb 132. Where the impact force is directed through the centerline of the body portion 120, the offset barb configuration provides a more acute angle of penetration than with non-offset barbs. It is believed that the offset barb configuration allows for easier tissue penetration by utilizing less force, and also allowing the relationship to the proximal anchor point 136 and the distal body end 121 to be geometrically enhanced allowing for increased tissue pull out force. In addition, it is believed that the offset allows less tissue cutting and stretching relative to the effective width of the two proximal anchor points 136. While the anchoring element 130 is shown with two offset barbs 131,132, it will be understood that the anchoring element 130 may have more barbs or fewer barbs, and the barbs configuration may vary.

The fastener 100 and components thereof may be made of any of various materials suitable for insertion into the human body. In various embodiments, the fastener 100 of the may be made of biocompatible material, such as stainless steel or titanium. In various exemplary embodiments, the fastener 100 may be made of an absorbable material, such as a polymer. Exemplary absorbable materials include homopolymers and copolymers of lactide, glycolide, polyglycolide, polylactide, or various combinations or mixtures thereof. It will be understood that there are various suitable polymers and that each exhibits different absorption rates, and different shear and tensile strengths when molded.

It will be understood that the fastener 100 will have dimensions suitable for insertion into the human body, and suitable to provide a stable anchoring structure. For example, in various embodiments, the fastener 100 may have an effective overall length (measured longitudinally from proximal end 102 to distal end 104) in the range of about 4 mm to about 6 mm. In the various embodiments, the diameter of the head portion 110 measured transversely at the widest point may be in the range of about 4 mm to about 10 mm In exemplary embodiments, the fasteners 100 may be adapted so that a plurality of fasteners 100 may be loaded for application by a drive apparatus 200. In various exemplary embodiments, one or more fasteners 100 may be loaded into a fastener drive apparatus 200 and inserted into the surgical field, either directly, as in the case of open surgery, or through a trocar cannula. The fasteners 100 should be sized to be compatible with the size of the drive apparatus 200 and associated devices. For example, the fasteners 100 may be sized to fit through different diameter tube assemblies, thus different size trocar ports. Smaller fasteners 100 enable the use of smaller tube assemblies. For example, small fasteners 100 having a diameter of about 4 mm make possible the use of a trocar cannula with a diameter as small as about 5 mm.

Turning now to FIGS. 5-14 a drive apparatus 200 according to an exemplary embodiment will be described. In various embodiments, drive apparatus 200 is configured to enable a user such as a surgeon to insert and secure a fastener 100 to a body tissue. Preferably, the drive apparatus 200 is configured for easy manipulation and one-handed use by a user. In an exemplary embodiment, one or more fasteners 100 may be loaded into the drive apparatus 200, so that they may be individually deployed by the drive apparatus 200. In exemplary embodiments, the drive apparatus 200 may have a sequencer or indexer 260 to align and shift the fasteners 100 inside the drive apparatus 200. The drive apparatus 200 further may have a driver mechanism 270 to provide a rapid impulse force to a fastener 100, ejecting the fastener 100 from the drive apparatus 200 with sufficient force to insert the fastener 100 into a body tissue.

Figure 10:
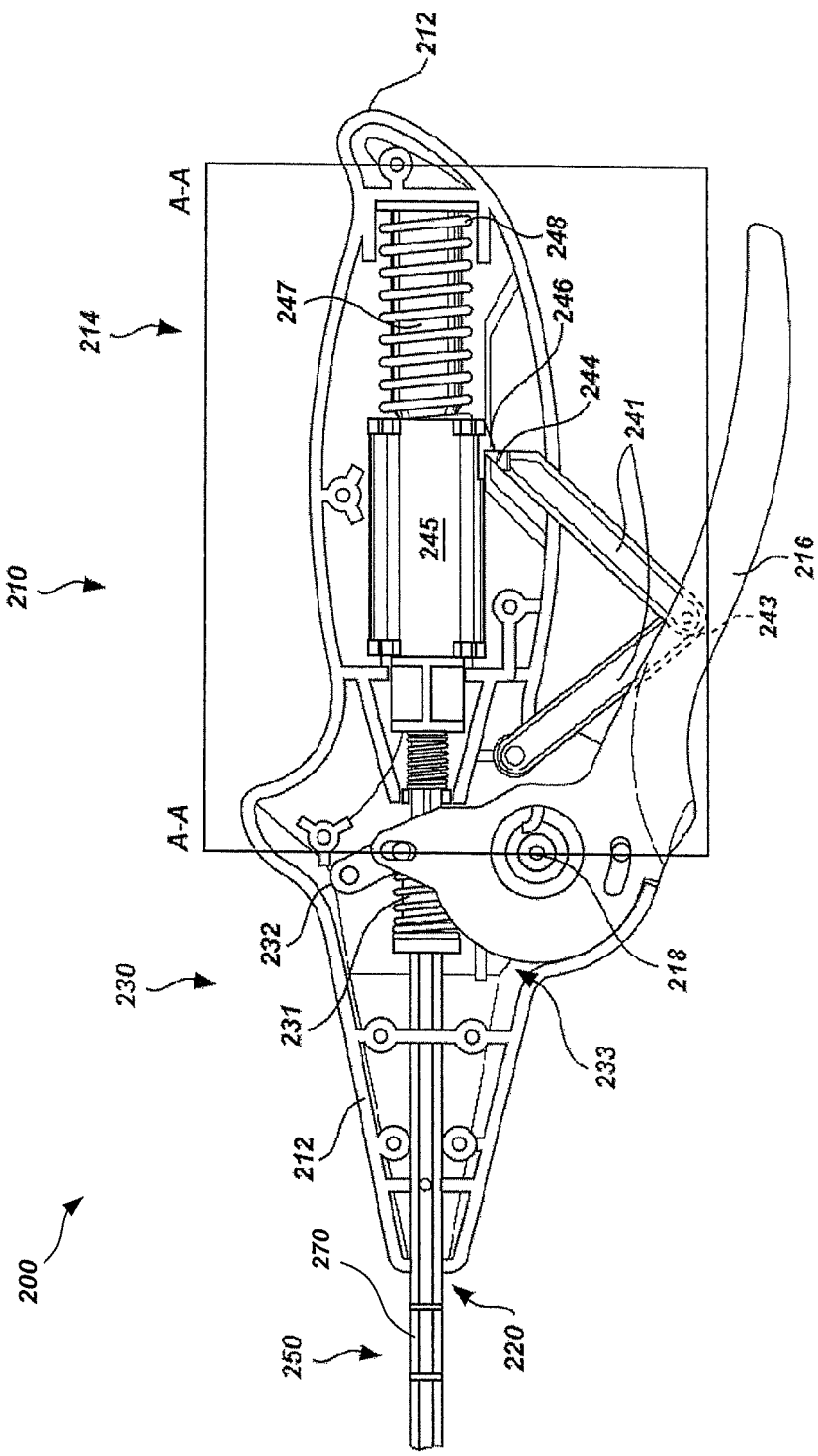
FIG. 10 is a partial sectional side view of a handle/actuation portion of a drive apparatus in an initial position, in accordance with an exemplary embodiment.

As illustrated in FIG. 10, in various exemplary embodiments, the drive apparatus 200 has a handle/actuation assembly 210 and a tube assembly 250. The tube assembly 250 may be configured to house a plurality of fasteners 100. The tube assembly 250 has a distal end 254, from which the fasteners 100 are ejected. The handle/actuation assembly 210 provides a handgrip 214 that enables the user to manipulate the drive apparatus 200. In exemplary embodiments, the handle/actuator assembly 210 further includes a trigger 216 that, when triggered, actuates the indexer 260, the driver mechanism 270, or both.

In exemplary embodiments, the tube assembly 250 has an elongated tube portion 252, extending in a longitudinal direction, $L_T$, and having a length Y. At its proximal end, the elongated tube portion 252 is joined with the handle/actuation assembly 210. The distal end of the elongated tube portion 252 coincides with the distal end 254 of the tube assembly 250, from which the one or more fasteners 100 are ejected. The length Y of the elongated tube portion 252, measured from its proximal end to its distal end, may be selected according to the intended use of the drive apparatus 200. For example, in an embodiment in which the drive apparatus 200 is used in laparoscopic procedures, the elongated tube portion 252 may have a length of about 12 inches to about 15 inches. In an embodiment in which the drive apparatus 200 is used for non-laparoscopic applications, a length of about 4 inches to about 9 inches may be more suitable. As guided by the disclosure herein, it will be understood by one of ordinary skill in the art how to select a suitable length for the elongated tube portion 252, depending on the intended use of the drive apparatus 200.

Turning now to FIGS. 5-9, the tube assembly 250 will be described in more detail. As illustrated in the figures, in various exemplary embodiments, the tube assembly 250 houses an indexer 260, a driver 270, and a spacer. Generally speaking, the indexer 260 serves the purpose of indexing the one or more fasteners 100 within the tube assembly 250, and moving them toward the distal end 254 of the tube assembly 250 so that they may be ejected. The driver 270 generally serves the purpose of ejecting the distal-most fastener 100 from the distal end 254 of the tube assembly 250. The spacer generally serves the purpose of aligning the driver 270, the indexer 260 within the tube assembly 250. Each of these devices is explained in more detail herein.

In various exemplary embodiments, the indexer 260 may have an elongated member 262 adapted to temporarily secure the fasteners 100 within the tube assembly 250, and to index the fasteners 100 in a distal direction along the longitudinal direction $L_T$ of the tube assembly 250. For example, the indexer 260 may have an elongated member 262 that is adapted to fit within the passage 115 of the one or more fasteners 100 loaded in the drive apparatus 200. It will be understood that in other exemplary embodiments, the elongated member 262 may be disposed along one or more sides of the fasteners 100, rather than through the central passage 115 of the fasteners 100.

In exemplary embodiments, the elongated member 262 may move in a direction substantially parallel to the longitudinal direction $L_T$ of the tube assembly 250. The elongated member 262 may have one or more features that enable it to transport the one or more fasteners 100 within the tube assembly 250. For example, the indexer 260 may further have a plurality of indexer engagers 264, 266, that temporarily secure the fasteners 100 to the indexer 260, so that the fasteners 100 move with the indexer 260. In the exemplary embodiment illustrated in FIG. 6, the indexer 260 has an elongated member 262 that is coupled with a distal index engager 264 and a proximal index engager 266. The elongated member 262 fits inside the passage 115 of one or more fasteners 100 (see FIGS. 5 and 7). The proximal index engager 266 is configured to engage with the proximal head face 112 of fastener 100. The distal index engager 264 is configured to temporarily engage with the distal head face 111 of fastener 100. In this configuration, the index engagers 264, 266, temporarily secure the fastener 100 to the elongated member 262 so that the fasteners 100 move with the elongated member 262.

In various embodiments, the indexer 260 may be configured to enable the fasteners 100 to move independently from the indexer 260. For example, index engagers 264, 266, may be configured to enable the fasteners 100 to slide in a distal direction along the elongated member 262, but prevent the fasteners 100 from moving in a proximal direction. In the exemplary embodiment illustrated in FIG. 6, the proximal index engager 266 has two angled arms 267 that extend toward the proximal head face 112 of the fastener 100. At its widest point, which is adjacent the proximal head face 112, the arms 267 render the proximal index engager 266 wider than the passage 115 of the fastener 100, providing a stop that prevents the proximal movement of the fastener 100 relative to the indexer 260. The arms 267 are sufficiently flexible to enable the fastener 100 to slide over the proximal index engager 266 in a distal direction. However, once the fastener 100 has slid past the proximal index engager 266, the arms 267 shift back to their initial configuration, preventing the proximal movement of the fastener 100 relative to the indexer 260. In the exemplary embodiment of FIG. 6, the distal index engager 264 has two arms 265 extending toward the distal head face 111 of the fastener 100. The arms 265 have rounded ends that are capable of limiting the distal movement of the fastener 100 relative to the indexer 260, but when a force that exceeds a predetermined threshold is applied to the fastener 100, the arms 265 flex inward, enabling the fastener 100 to slide in a distal direction over the distal index engager 264. It will be understood how to specify the predetermined threshold, consistent with the guidance provided herein.

In various exemplary embodiments, the tube assembly 250 may be configured to limit the proximal movement of the fasteners 100 relative to the tube assembly 250. In the exemplary embodiment illustrated in FIG. 6, the elongated tube portion 252 may have, along its inner surface, one or more lance tabs 256 that provide an interference point along the elongated tube portion 252, preventing the proximal movement of the fasteners 100 relative to the elongated tube portion 252. For example, in the embodiment illustrated in FIG. 6, lance tabs 256 project from the inner surface of the elongated tube portion 252, at an angle toward the distal end of the elongated tube portion 252. At its distal end, the lance tabs 256 reduces the width of the elongated tube portion 252 so that it is narrower than the width of the head portion 110 of the fastener 100, providing a stop that prevents the fastener 100 from moving in a proximal direction relative to the elongated tube portion 252. However, the lance tabs 256 are capable of flexing outward when the fastener 100 slides past them in a distal direction. In exemplary embodiments, the lance tabs 256 may be provided in pairs, disposed on opposite sides of the elongated tube portion 252. In certain embodiments, the lance tabs 256 are made of punch-outs on the elongated tube portion 252, that are flexed or bent toward the center of the elongated tube portion 252. In this configuration, the lance tabs 256 are integral with the elongated tube portion 252. However, it will be understood that the lance tabs 256 may be separately formed, and attached to the inner surface of the elongated tube portion 252, to provide projections, flanges, or other suitable structures along the interior of the elongated tube portion 252. It will be understood that other features may be provided as an alternative to, or in addition to the lance tabs 256, to limit the proximal movement of the fasteners 100 relative to the elongated tube portion 252.

Figure 5:
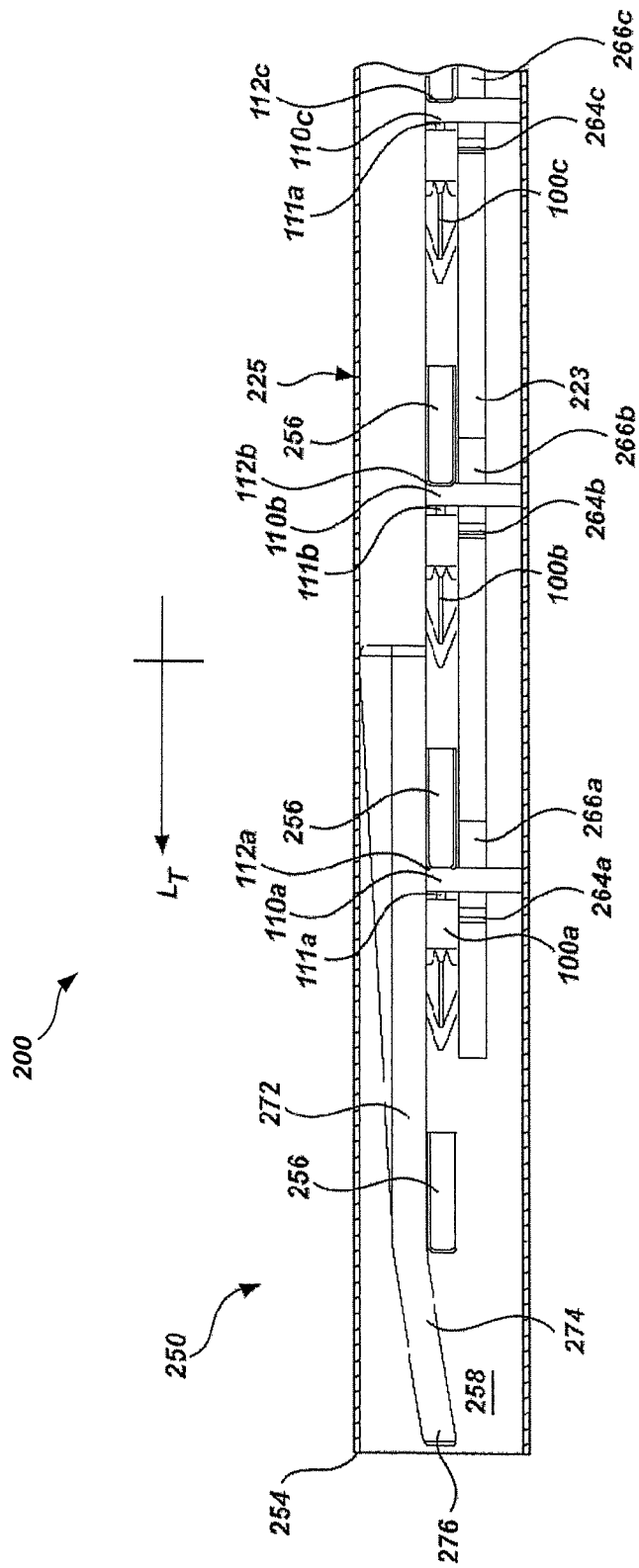
FIG. 5 is a partial sectional side view of a tube assembly of a drive apparatus and fasteners, in accordance with an exemplary embodiment.
Figure 6:
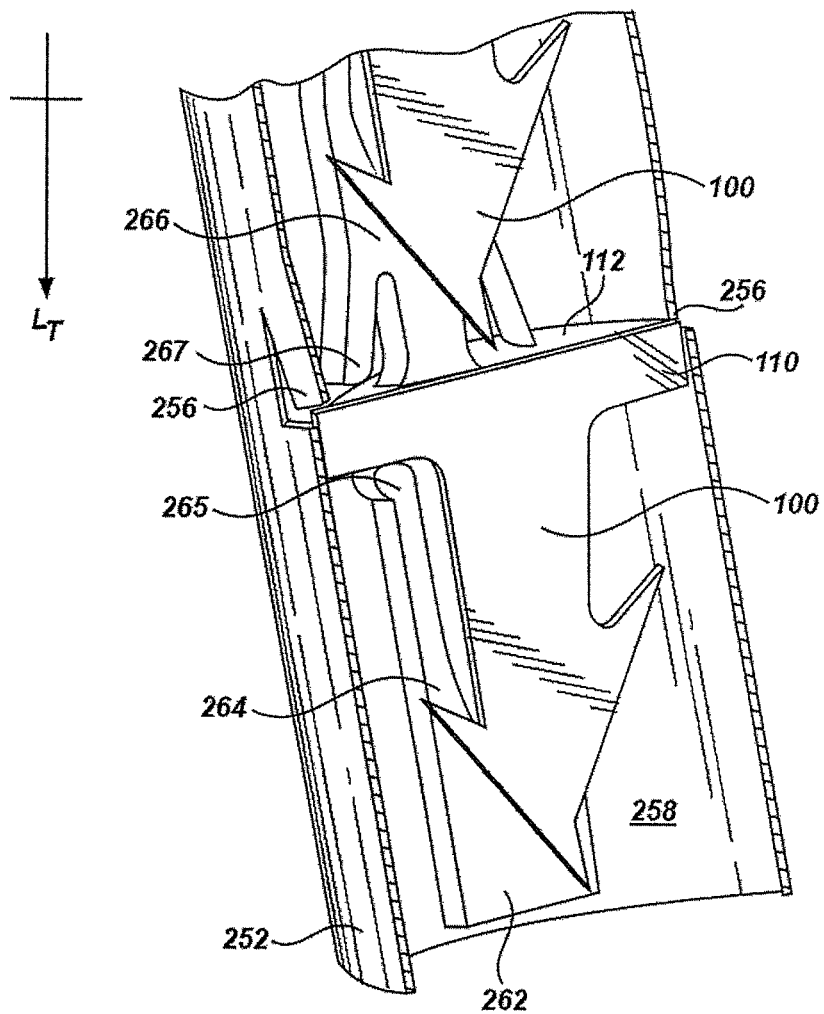
FIG. 6 is a partial sectional perspective view of a distal portion of a tube assembly of a drive apparatus and fasteners, in accordance with an exemplary embodiment.
Figure 7:
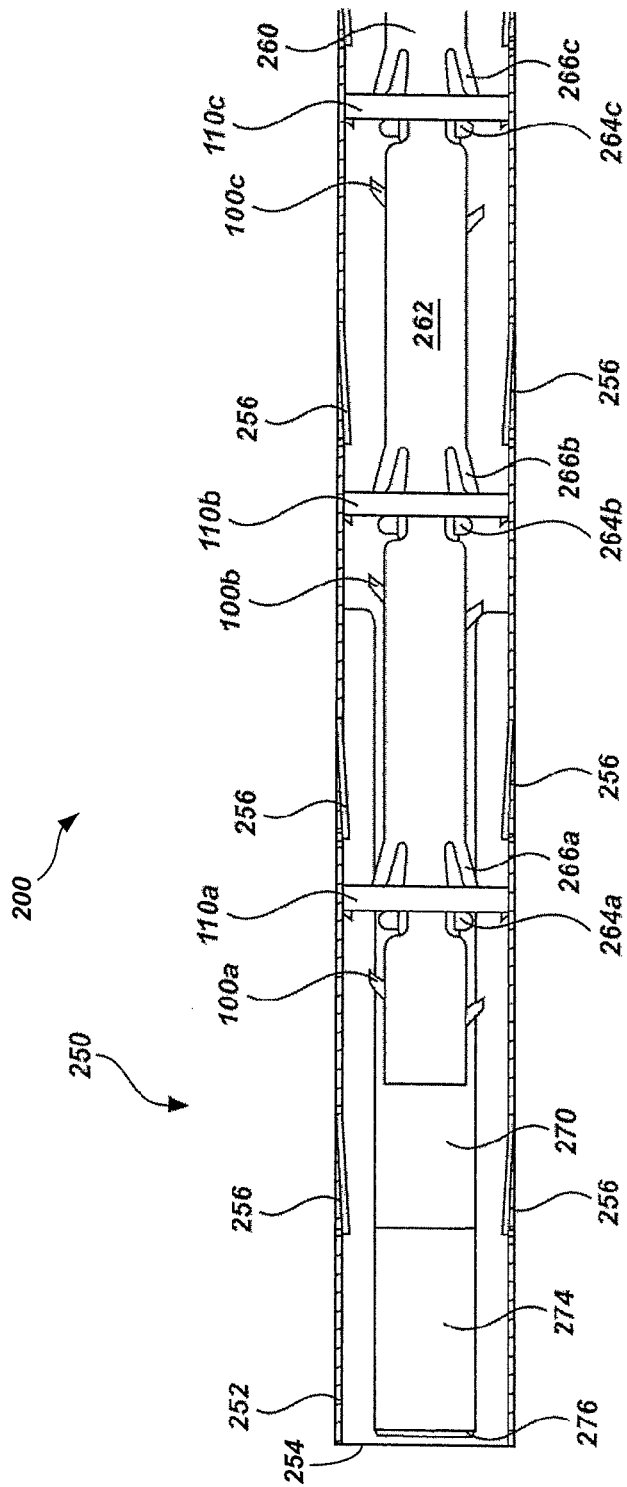
FIG. 7 is a partial sectional bottom view of a distal portion of a tube assembly of a drive apparatus and fasteners, in accordance with an exemplary embodiment.

In various exemplary embodiments the indexer 260 is configured to index multiple fasteners 100 within the elongated tube portion 252. FIG. 5 illustrates a side elevation view of an exemplary tube assembly 250, with a portion of the elongated tube portion 252 cut away to reveal the internal elements. FIG. 7 illustrates a bottom view of an exemplary tube assembly 250, with a portion of the elongated tube portion 252 cut away to reveal the internal elements. In these exemplary embodiment, three fasteners 100a, 100b, and 100c are shown, but it will be understood that the drive apparatus 200 may be configured to hold more, or fewer, fasteners 100. Indexer 260 preferably has a number of proximal index engagers 266, and distal index engagers 264 that is equal to or greater than the number of fasteners 100 loaded in the drive apparatus 200, so that each fastener 100 is secured to the indexer 260 prior to being expelled from the drive apparatus 200. Indexer 260 has an elongated member 262, that extends through the passage (not shown) of the respective head portions 110a, 110b, 110c, of each of the fasteners 100a, 100b, 100c. Adjacent the distal head face (111a, 111b, 111c) of each head portion is a distal index engager 264a, 264b, 264c, and adjacent each proximal head face (112a, 112b, 112c) is proximal index engager 266a, 266b, 266c. Lance tabs 256 are located on the inner surface of the elongated tube portion 252, and are shown abutting the proximal head faces (112a, 112b, 112c) of the fasteners 100a, 100b, 100c.

Figure 8:
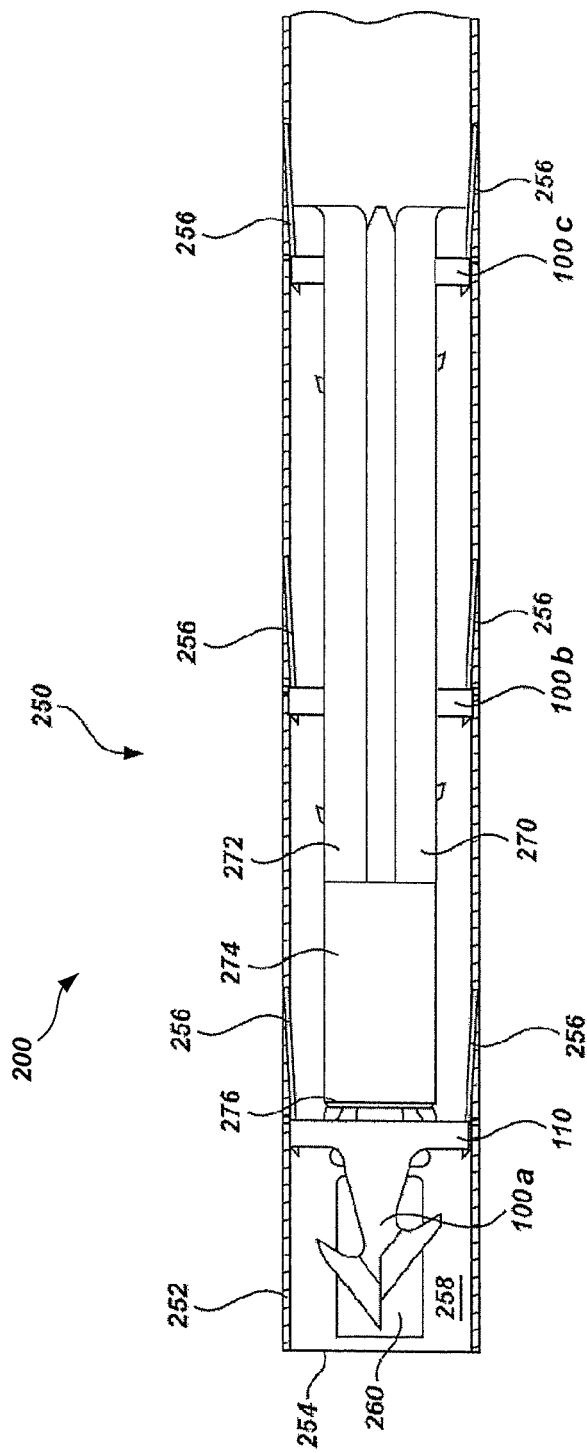
FIG. 8 is a partial sectional top view of a distal portion of a tube assembly of a drive apparatus and fasteners, in accordance with an exemplary embodiment.

The operation of the indexer 260 will now be described in reference to the embodiments of FIGS. 5, 7, and 8. For purposes of discussion, the indexer 260 in FIGS. 5 and 7 is illustrated in its initial, proximal-most position (i.e., the position it holds during the initial stage of operation), which is also its reset position; the indexer 260 in FIG. 8 is illustrated in its distal-most position, which is its position at the pre-firing stage. From this position, the indexer 260 may be described as having a cyclical movement, during which it may move distally from its initial position to its pre-firing stage position (the distal stroke) and then proximally back to the initial position (the proximal stroke), completing a full cycle of movement.

In an exemplary embodiment, during the indexer's 260 distal stroke, the indexer 260 moves the fasteners 100a, 100b, and 100c which are held in place by the respective index engagers 264a-c and 266a-c. The distal stroke of the indexer 260 may end when the fasteners 100a, 100b, 100c advance beyond the next lance tab 256, as illustrated in FIG. 8. This places the distal-most fastener 100a in its firing position relative to the tube assembly 250; i.e., the position at which it is ready to be ejected from the tube assembly 250, such as by driver 270. After the indexer 260 reaches its pre-firing stage position, it may commence its proximal stroke. During the indexer's 260 proximal stroke, the lance tabs 256 prevent the proximal movement of the fasteners 100a, 100b, 100c relative to the tube assembly 250, as described above. Therefore, the proximal movement of the indexer 260 creates a force between the distal index engagers 264a, 264b, 264c, and the respective distal head faces 111a, 111b, 111c. When this force reaches a certain threshold, the distal index engagers 264a, 264b, 264c will flex inward and slide through the passage (not shown) of the respective fastener 100a, 100b, 100c, enabling the indexer 260 to continue its proximal stroke without moving the fasteners 100a, 100b, 100c. The indexer's 260 proximal stroke continues until index engagers 264a-c and 266a-c, engage with the next proximal fastener (e.g., index engagers 264a and 266a may engage with next proximal fastener 100b, and index engagers 264b and 266b may engage with next proximal fastener 100c, etc.) At this point, the indexer 260 has returned to its initial position, completing a full cycle. In exemplary embodiments, the length of the distal stroke of the indexer 260 is about equal to the distance between adjacent lance tabs 256. The indexer 260 may repeat this cycle one or more times, advancing all of the fasteners 100 distally within the tube assembly 250 as described above.

In exemplary embodiments, the indexer 260 is operably coupled with the handle/actuation assembly 210 so that movement of the indexer 260 is controlled by one or more mechanisms within the handle/actuation assembly 210, which is described in more detail below.

In various embodiments, the driver assembly 200 has a driver 270 that is configured to provide an ejection force to a fastener 100, expelling the fastener 100 from the distal end 254 of the tube assembly 250. In exemplary embodiments, the vector of the ejection force is substantially parallel to the longitudinal direction $L_T$ of the tube assembly 250, and the force is applied to the fastener 100 so that the fastener 100 is expelled in a direction that is substantially parallel to the longitudinal direction $L_T$ of the tube assembly 250. In exemplary embodiments, the ejection force is sufficient to insert the fastener 100 into a body tissue. In certain embodiments, the ejection force is an impulse force that fires the fastener 100 from the distal end 254 of the tube assembly 250.

As illustrated in FIG. 5, in various exemplary embodiments the driver 270 may be an elongated member, such as a beam or shaft, that terminates on its distal end at an ejector portion 276. The elongated driver member may have a rectangular cross section; however, it will be understood that the elongated driver member may have any of a number of suitable different shapes and configurations. In exemplary embodiments, the elongated member of the driver 270 may have a straight portion 272, an angular portion 274 that is angled downward toward the ejector portion 276. In this configuration, the straight portion 272 of the driver 270 may be offset from the pathway of movement of the fasteners 100a, 100b, 100c, while the ejector portion 276 delivers the ejection force along the pathway of movement of the fasteners 100a, 100b, 100c. It will be understood that the driver 270 may have other physical configurations consistent with its function of delivering the ejection force to the fasteners 100a, 100b, 100c.

Figure 9:
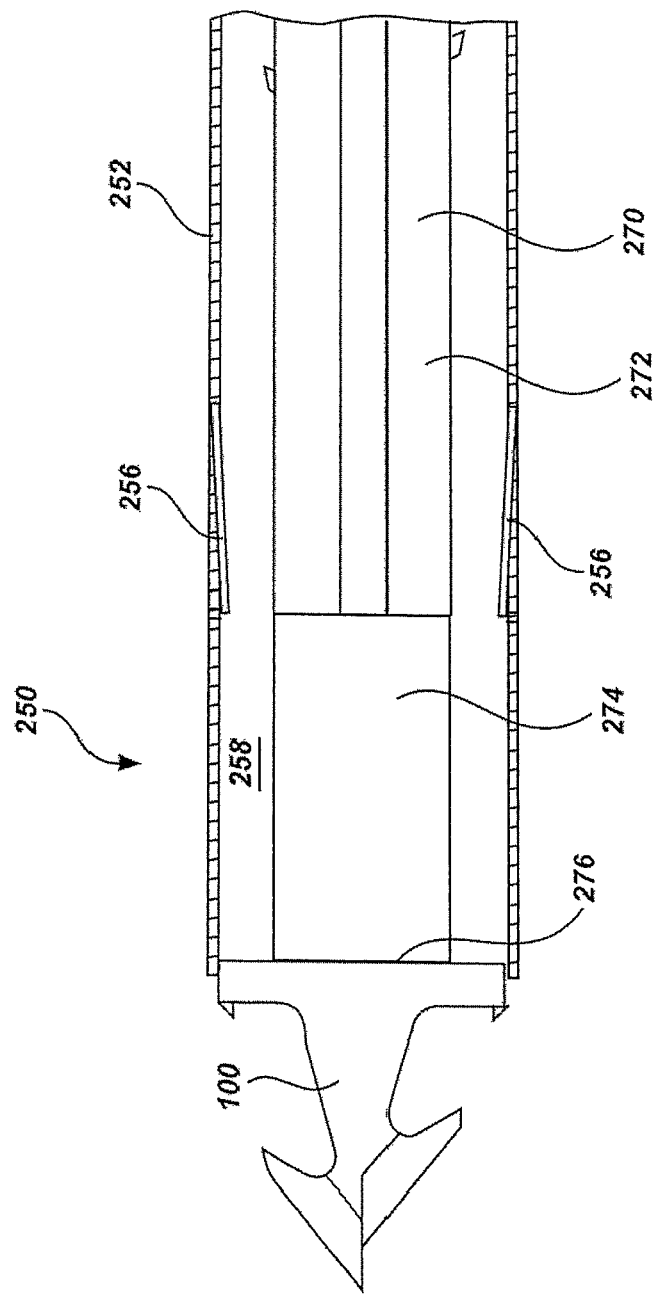
FIG. 9 is a partial sectional top view of a distal portion of a tube assembly of a drive apparatus and fastener, in accordance with an exemplary embodiment.

The operation of the driver 270 will now be described in reference to the embodiments of FIGS. 5, 7, 8, and 9. For purposes of discussion, the driver 270 in FIGS. 5 and 7 is illustrated in its initial position (also the reset position); the driver 270 in FIG. 8 is illustrated in its pre-firing position, and the driver 270 in FIG. 9 is illustrated in its firing position. From its initial position, the driver 270 is at or near its distal-most position. From this position, the driver 270 may be described as having a cyclical movement, during which may move proximally toward the handle/actuation assembly 210 of the driver apparatus 200 (the proximal stroke) and then distally back to the initial position (the distal stroke), completing a full cycle of movement. In exemplary embodiments, the driver 270 may move in a direction substantially parallel to the longitudinal direction $L_T$ of the tube assembly 250.

In the exemplary embodiment illustrated in FIG. 5, the driver 270 is shown in its initial position (also reset position) with the ejector portion 276 of the driver 270 adjacent the distal end 254 of the tube assembly 250. During its proximal stroke, the driver 270 retracts away from the firing position 258 of the tube assembly 250, while the indexer 260 indexes the distal-most fastener 100 into the firing position 258. At the end of its distal stroke, driver 270 is in its pre-firing position, as illustrated in FIG. 8. In the pre-firing position, ejector portion 276 of the driver 270 is adjacent to the proximal head surface 112 of the fastener 100 that is in the firing position 258. During its distal stroke, the driver 270 delivers an ejection force (e.g., an impulse force) to the distal-most fastener 100 located in the firing position 258. As illustrated in FIG. 9, when the driver 270 is in its firing position, it is ejecting this fastener 100 from the distal end 254 of the tube assembly 250. In exemplary embodiments, the driver 270 ejects the fastener 100 with sufficient force and speed that the fastener 100 is securely inserted into the surgical field, such as into a hernia mesh or a body tissue. Once the fastener 100 is ejected by the driver 270, the driver 270 is in its initial position (or reset position), as illustrated in FIGS. 5 and 7, As illustrated in FIG. 5, the driver 270 may be disposed near the upper portion of the elongated tube portion 252, so that it is above the indexer 260, and fasteners 100. In this configuration, the straight portion 272 of the elongated member is generally disposed above the fasteners 100. In various embodiments, the ejector portion 276 of the driver 270 may move up and down during the driver's 270 cycle of movement. For example, in the driver's 270 proximal stroke, the driver 270 may flex or pivot upward from its initial position so that the ejector portion 276 moves out of the indexing pathway of fasteners 100. During the distal stroke of the driver 270, the ejector portion 276 may drop down behind the fastener 100 that is in the firing position 258, so that the ejector portion 276 pushes the fastener 100 along a path of movement that is parallel to the longitudinal direction $L_T$ of the tube assembly 250.

While the embodiments thus far have been described with respect to a driver 270 that is located above the fasteners 100, it will be understood that the driver 270 may be located instead in a different area or region, such as above or to one or more sides of the fasteners 100, or the driver 270 may be aligned with the path of movement of the fasteners 100.

In exemplary embodiments, the direction and speed of the movement of the driver 270 is independent of the movement of the indexer 260. For example, the driver 270 may be in its distal stroke when the indexer 260 is in its proximal stroke. In addition, during their respective distal strokes, the rate of speed of the driver 270 may be faster than the speed of the indexer 260.

In exemplary embodiments, the driver 270 is operably coupled with the handle/actuation assembly 210 so that movement of the driver 270 is controlled by one or more mechanisms within the handle/actuation assembly 210, which is described in more detail below.

In exemplary embodiments, the drive apparatus 200 may have a spacer disposed with in the tube assembly 250, in the elongated tube portion 252. The spacer may be configured to maintain the alignment of the driver 270, the indexer 260, and the fasteners 100, within the elongated tube portion 252. In exemplary embodiments, the spacer is stationary relative to the elongated tube portion 252. However, it will be understood that the spacer may move relative to one or more components of the tube assembly.

As previously indicated, the drive apparatus 200 may have a handle/actuation assembly 210 that provides a housing 212, a handgrip portion 214, and a trigger 216. FIG. 10 illustrates a section view of a handle/actuation assembly 210 according to an exemplary embodiment. The housing 212 defines an interior space that houses the mechanical elements of the handle/actuation assembly 210. It will be understood that only one side of the housing 212 is illustrated in FIG. 10, and that the complete housing 212 may include a mirror image portion, fastened to the illustrated portion, such as by screws or other mechanical fasteners, or by welding. The distal end of the housing 212 has a tube assembly opening 220, through which the tube assembly 250 is inserted so that it may be operably coupled with one or more mechanical elements inside the housing 212. The proximal portion of the handle/actuation assembly 210 comprises a handgrip portion 214, which is configured for easy manipulation for a user. It will be understood how to design the handgrip portion 214 with various contours and features suitable for this purpose.

In exemplary embodiments, a trigger 216 is pivotably coupled with the handle/actuation assembly 210 at trigger pivot 218, located at least partially within housing 212. Trigger 216 may be configured so that it may be easily manipulated by a user from outside of the housing. For example, in the embodiment illustrated in FIG. 10, the trigger 216 may be a lever arm adjacent the handgrip portion 214. The trigger 216 may be manipulated by the user, for example, by squeezing the lever arm toward the handgrip portion 214, causing the trigger 216 to rotate in a counter-clockwise direction about trigger pivot 218. It will be understood that trigger 216 may comprise one of various other triggering devices now known or later developed, consistent with the teachings provided herein. In exemplary embodiments, trigger 216 is biased toward the untriggered position. For example, the trigger 216 may be biased by using a torsion spring, a spring clip, or other suitable devices. One of ordinary skill in the art would be able to design and configure various devices suitable for biasing the trigger 216, using the guidance provided herein.

In exemplary embodiments, trigger 216 is operably coupled with at least one actuator, such that manipulation of the trigger 216 actuates the indexer 260, the driver 270, or both. In exemplary embodiments, trigger 216 is operably coupled with an indexer actuator assembly 230 that is operably coupled with (either directly or indirectly) the indexer 260. In exemplary embodiments, trigger 216 is operably coupled with a driver actuator assembly 240 that is operably coupled with (either directly or indirectly) the driver 270. In the various embodiments, indexer actuator assembly 230 and driver actuator assembly 240 are disposed at least partially within housing 212, and are operably coupled with the tube assembly 250, which at least partially extends from the tube opening 220 in housing 212.

Figure 12:
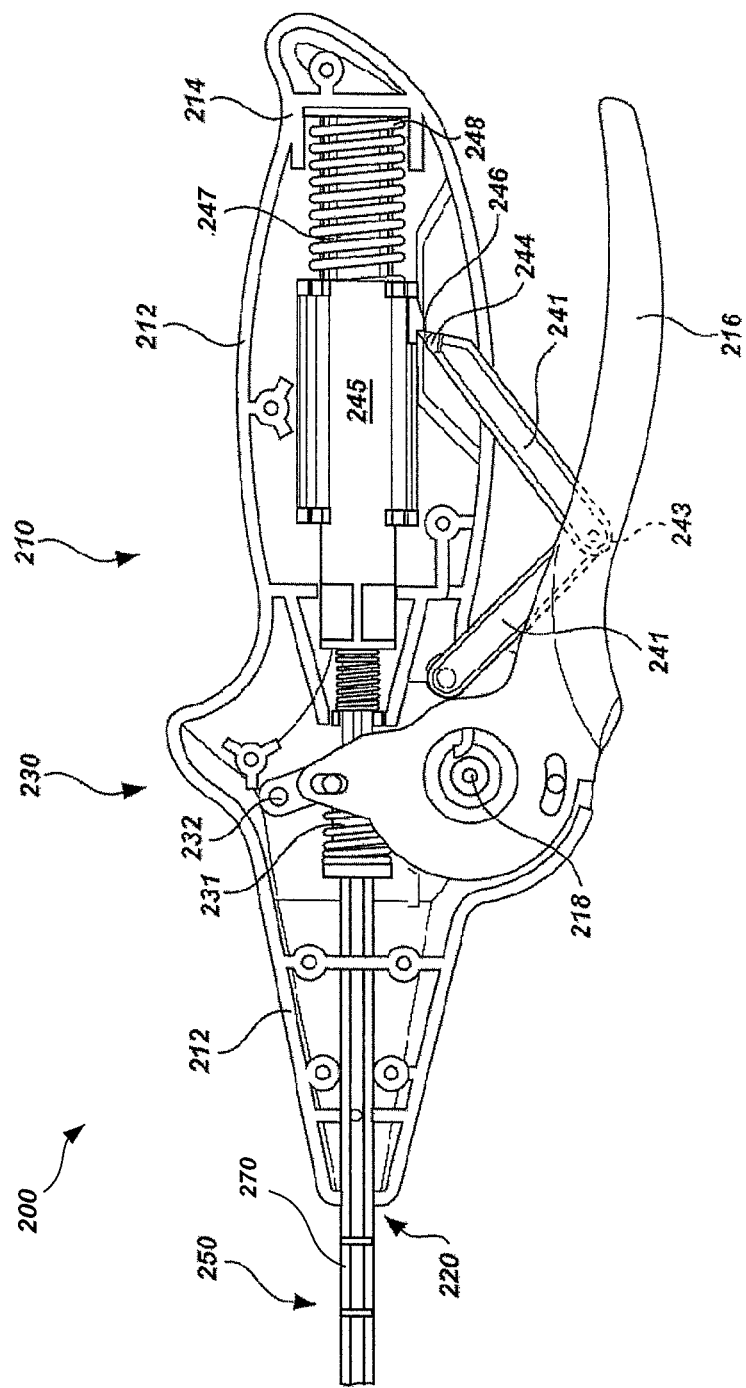
FIG. 12 is a partial sectional side view of a handle/actuation portion of a drive apparatus in an intermediate position in accordance with an exemplary embodiment.
Figure 13:
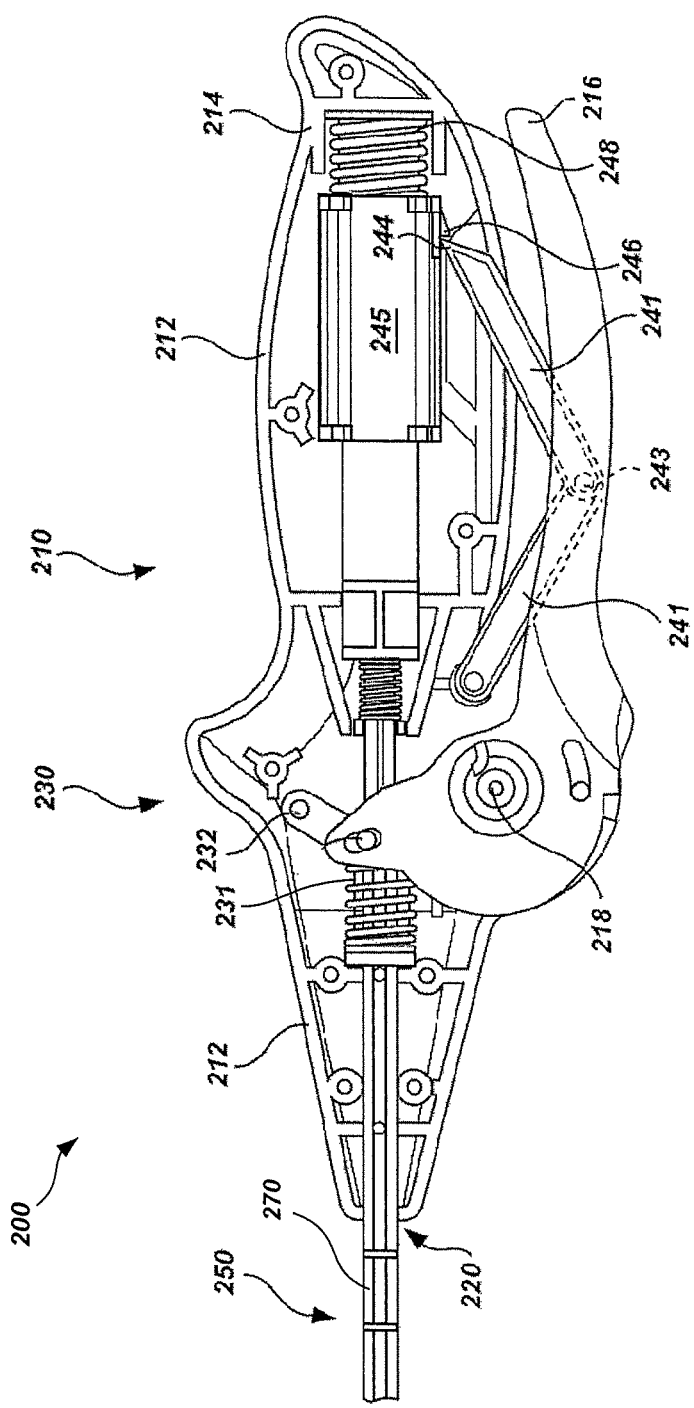
FIG. 13 is a partial sectional side view of a handle/actuation portion of a drive apparatus in a pre-fired position in accordance with an exemplary embodiment.

In exemplary embodiments, indexer actuator assembly 230 is operably coupled with the indexer 260, to provide the mechanical action necessary to move the indexer 260 through its full cycle of motion. The indexer actuator assembly 230 of an exemplary embodiment will now be described with reference to FIGS. 10-13. In exemplary embodiments, the indexer actuator assembly 230 includes a cam 232 that is operably coupled with the trigger 216 and translates the rotational movement of the trigger 216 about the trigger pivot 218, into longitudinal movement of pusher aim 231. FIG. 10 illustrates the exemplary indexer actuator assembly 230 at or near its initial position (also its reset position), in which the trigger 216 has not been squeezed, and the pusher arm 231 is at its proximal-most position. In the exemplary embodiment, as trigger 216 is squeezed, the trigger 216 pivots in a counter clockwise direction about trigger pivot 218. When the trigger 216 pivots, the cam 232 causes the pusher arm 231 to move in a distal direction. FIG. 12 illustrates the exemplary indexer actuator assembly 230 in this intermediate position, in which the trigger 216 has been squeezed, so that it has partially rotated about trigger pivot 218, and cam 232 has engaged with pusher arm 231 to push it in a distal direction. The indexer 260 is operably coupled with indexer actuator assembly 230, such that distal movement of the pusher arm 231 causes distal movement of the indexer 260 (i.e., the distal stroke of the indexer 260). When the trigger 216 is fully squeezed, as illustrated in FIG. 13, the pusher arm 231 reaches its distal-most position, and the indexer 260 completes its distal stroke. When the trigger 216 is thereafter released, a biasing force acts on the indexer actuator assembly 230 to move the pusher arm 231 in a proximal direction, thereby causing the indexer 260 to move in its proximal stroke. The biasing force may be provided by one or more biasing devices that are operably coupled with the trigger 216, the trigger pivot 218, the cam 232, the pusher arm 231, or any combination thereof. The biasing force is sufficient to return the pusher arm 231 (and therefore the indexer 260) to its initial position (e.g., FIG. 10).

In exemplary embodiments, drive actuator assembly 240 is operably coupled with the driver 270, to provide the mechanical action necessary to move the driver 270 through its full cycle of motion. The driver actuator assembly 240 of an exemplary embodiment will now be described with reference to FIGS. 10-13. In exemplary embodiments, the driver actuator assembly 240 includes a slideable plunger 245 that is slidably coupled with a central shaft 247, so that the plunger 245 may move in a proximal and distal direction along the shaft 247. FIG. 10 illustrates the exemplary driver actuator assembly 240 at or near its initial position (or reset position), in which the pusher arm 245 is at its distal-most position. The driver 270 may be coupled with the driver actuator assembly 240 such that proximal movement of the slideable plunger 245 causes proximal movement of the driver 270 (e.g., its proximal stroke), and distal movement of the slidable plunger 245 causes distal movement of the driver 270 (e.g., its distal stroke). A biasing spring 248 biases the plunger 245 toward the distal end of the shaft 247, and therefore biases the driver toward the distal end 254 of the tube assembly 250.

Figure 14:
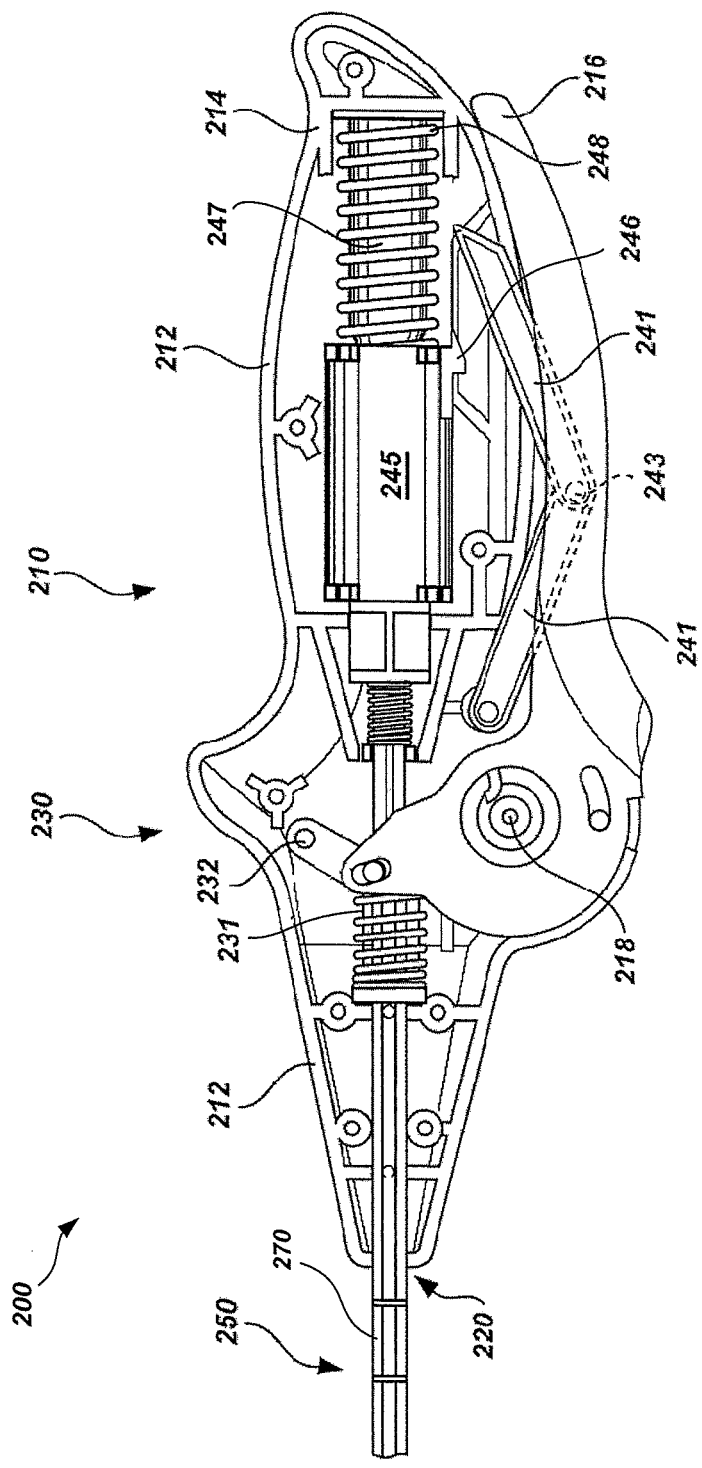
FIG. 14 is a partial sectional side view of a handle/actuation portion of a drive apparatus in a post-fired position in accordance with an exemplary embodiment.

In exemplary embodiments, the slideable plunger 245 of driver actuator assembly 240 is operably coupled with the trigger 216, so that the squeezing the trigger 216 moves the slideable plunger 245 (and likewise the driver 270) in a proximal direction. For example, scissor beams 241 may be attached at one end to the handle/actuation assembly 210, such as at a beam pivot 242; the free end 244 of the scissor beams 241 may be operably coupled with the proximal end of the slideable plunger 245, such as at lip 246. The scissor beams 241 are joined at elbow joint 243, and are biased toward a closed position, such as with a torsion spring or other suitable device. Elbow joint 243 may be operably coupled with the trigger 216, such that squeezing of the trigger 216 causes the scissor beams 241 to straighten at the elbow joint 243, so that the free end 244 of the beams 241 pushes on the lip 246 of the slideable plunger 245, causing plunger 245 to slide in a proximal direction along shaft 247. FIG. 12 illustrates the driver actuator assembly 240 in an intermediate position, in which the trigger 216 has not been fully squeezed, the scissor beams 241 are partially straightened or extended, and the plunger 245 has moved in a proximal direction along the central shaft 247. The proximal movement of the plunger 245 causes the driver 270 to move along its proximal stroke. When the trigger 216 is fully squeezed, the plunger 245 reaches a pre-firing position (illustrated in FIG. 13), at which point the plunger 245 is at its proximal-most point and the beams 241 are still engaged with the lip 246. After the driver actuation assembly 240 reaches the pre-firing position, when the trigger 216 is further squeezed, the beams 241 are configured to automatically disengage from the plunger 245, enabling the biasing spring 248 to force the plunger 245 to slide in a distal direction. FIG. 14 illustrates the driver actuator assembly 240 in a post-firing position, just after the scissor beams 241 have released from the plunger 245, and the plunger 245 has moved in a distal direction along central shaft 247. The distal movement of the plunger 245 causes the driver 270 to move along its distal stroke, thereby "firing" fastener 100, or ejecting it from the distal end 254 of the tube assembly 250. In exemplary embodiments the biasing spring 248 is configured to deliver an impulse force to the plunger 245 toward its initial distal-most position. This impulse movement is translated along the driver 270, to the ejector portion 276 of the driver 270, which delivers the impulse force to the fastener 100 that is in the firing position 258 within the tube assembly 250, thereby ejecting the fastener 100 with sufficient force to insert the fastener 100 into the surgical field, such as through a hernia mesh or body tissue. One of ordinary skill in the art would understand how to configure spring 248 to exert such a force, and would be able to apply such a spring to a drive apparatus 200, using the guidance provided herein.

Figure 11:
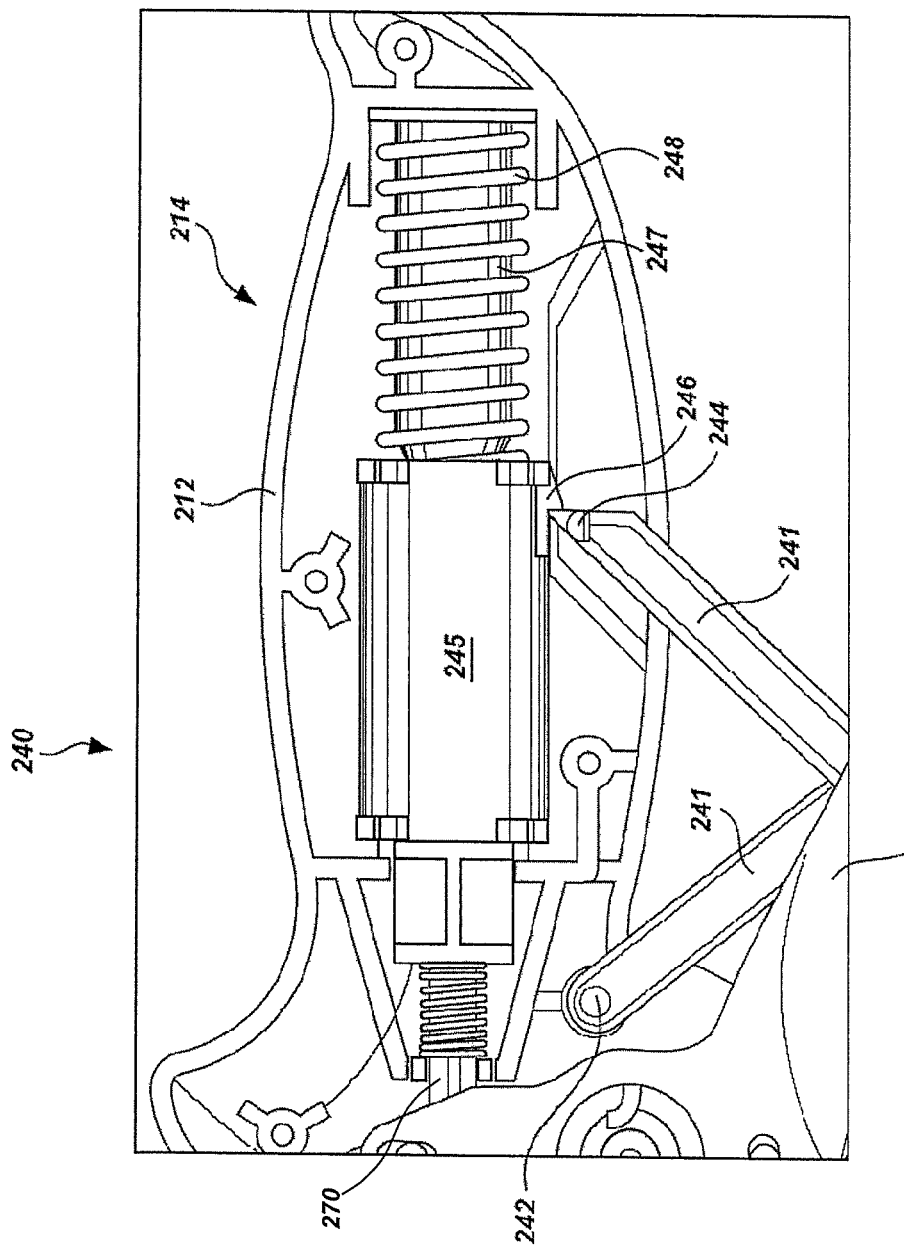
FIG. 11 is an enlargement of portion A-A of FIG. 10, in accordance with an exemplary embodiment.

In various exemplary embodiments, when the trigger 216 is released after it has been fully squeezed (so as to deliver the impulse force), the driver actuation assembly 240 returns to its initial position, as illustrated in FIGS. 10 and 11. During the return to the initial position, the scissor beams 241 return to their initial position, and the free end 244 of the beams 241 automatically re-engages with the lip 246 of plunger 245, so that the driver actuator assembly 240 is ready for another cycle of motion.

In various exemplary embodiments, the handle/actuation assembly 210 also includes a trigger lock 233, that prevents the trigger 216 from being released before it reaches its fully squeezed position, which may cause the inadvertent sequencing of fasteners 100, and release of the driver 270. For example, the trigger lock 233 may include a device that mechanically interferes with the rotation of the trigger 216 about pivot 218. One of ordinary skill in the art will understand the various devices that could be used as a trigger lock, and would be able to apply them to the handle/actuation assembly 210 using the guidance provided herein.

In exemplary embodiments, trigger 216 is operably coupled with both indexer actuator assembly 230, and driver actuator assembly 240, so that manipulation of the trigger 216 actuates both assemblies 230, 240. In various embodiments, the indexer 260 and driver 270 are independently coupled with the trigger 216 so that the driver 270 and the indexer 260 may be moved independently of each other when the trigger 216 is triggered. However, in exemplary embodiments, from the perspective of the user, the triggered actions of the drive apparatus 200 may appear to be simultaneous.

The method of operation of the drive apparatus 200 to deploy a fastener 100 may best be understood in reference to the exemplary embodiments illustrated in FIGS. 10-14. In exemplary embodiments, the drive apparatus 200 is manually operated by a user, such as a surgeon, who manipulates the drive apparatus 200 such as by grasping the handgrip portion 214, so as to position the distal end 254 of the tube assembly 250 adjacent the location where the fastener 100 is to be inserted. The user then squeezes the trigger 216, pulling it toward the handgrip portion 214, which causes the drive apparatus 200 to advance through a series of stages of operation described in more detail below.

FIG. 10 illustrates an exemplary drive apparatus 200 in its initial stage, in which the trigger 216 has not been squeezed. In its initial position, plunger 245 of driver actuator assembly 240 is in its distal-most position, and corresponding driver 270 is in its distal-most position, with ejector portion 276 adjacent the distal end 254 of tube assembly 250. In its initial position, pusher arm 231 of the indexer actuator assembly 230 is in its proximal-most position, and corresponding indexer 260 is in its proximal-most position. In the initial position, no fastener 100 is in the firing position 258 of the tube assembly 250.

In the exemplary embodiment, as the trigger 216 is squeezed, the drive apparatus 200 moves into an intermediate stage, illustrated in FIG. 12. In the intermediate position, plunger 245 of driver actuator assembly 240 has moved in a proximal direction, and corresponding driver 270 has progressed into its proximal stroke, in which the ejector portion 276 of the driver 270 moves away from the distal end 254 of tube assembly 250. In its intermediate position, pusher arm 231 of the indexer actuator assembly 230 has moved in a distal direction, and corresponding indexer 260 has moved in a distal direction within the tube assembly 250, indexing fasteners 100 in a distal direction toward the distal end 254 of the tube assembly 250.

Just prior the trigger 216 being fully squeezed, the drive apparatus 200 moves into a pre-firing stage, illustrated in FIG. 13. In the pre-firing position, pusher arm 231 of the indexer actuator assembly 230 is in its distal-most position, and corresponding indexer 260 has finished its distal stroke, so that the distal-most fastener 100 is in the firing position 258 within the tube assembly 250. In the pre-firing position, plunger 245 of the driver actuator assembly 240 has moved to its proximal-most position, and corresponding driver 270 has completed its proximal stroke, whereby the ejector portion 276 of the driver 270 is located adjacent the proximal head face 112 of distal-most fastener 100.

Just past the pre-firing position, as the user continues to squeeze the trigger 216 to its fully squeezed position, the scissor beams 241 release from lip 246 of plunger 245. Once released, the plunger 245 retracts to its distal-most position, under the compressive force of spring 248. This motion causes the corresponding driver 270 to fire or eject the distal-most fastener 100 that has been loaded by indexer 260 into the firing position 258 of tube assembly 250. In the exemplary embodiment, after the trigger 216 is fully squeezed, and the driver 270 fires the distal-most fastener 100 from the tube assembly 250, the drive apparatus 200 moves into a post-firing stage, illustrated in FIG. 14. In the post-firing position, scissor beams 241 have released plunger 245, which has retracted to its distal-most position, and corresponding driver 270 has ejected the distal-most fastener 100 from the firing position 258, through the distal end 254 of the tube assembly 250. In the post-firing position, the pusher arm 231 of the indexer actuator assembly 230 is at or near its distal-most position, and corresponding indexer 260 is at or near its distal-most position.

In the exemplary embodiment, when the trigger 216 is released after being fully squeezed, the drive apparatus 200 returns to its initial position, illustrated in FIG. 10. When released, the driver actuator assembly 240 returns to its initial position with the plunger 245 in its distal-most position, and the scissor beams 241 retract to their initial position, re-engaging with the plunger 245. When released, trigger 216 rotates in a clockwise direction about trigger pivot 218, and cam 232 and pusher arm 231 move in a proximal direction until pusher arm 231 reaches its proximal-most position. When pusher arm 231 moves in the proximal direction, the indexer 260 completes its proximal stroke until the indexer engagers 264, 266 engage with the next proximal fasteners 100.

From the perspective of the user, the triggered actions of the drive apparatus 200 appear to be simultaneous. In other words, the user places the distal opening 254 of the tube assembly 250 adjacent the portion of the hernia mesh to be fastened and squeezes the trigger 216 to its fullest extent in one continuous motion. This causes the distal fastener 100 to be ejected from the tube assembly 250 and into the hernia mesh and underlying body tissue. Upon release of the trigger 216, the drive apparatus 200 returns to its initial position and is immediately ready to dispense another fastener 100.

Many embodiments and adaptations of the present invention, other than those herein described with reference to the exemplary embodiments, will be apparent to those skilled in the art by the foregoing description, without departing from the substance or scope of the invention. While the present invention has been described herein in detail in relation to its exemplary embodiments, it is to be understood that this disclosure is only illustrative and exemplary of the present invention. Accordingly, the foregoing disclosure is not intended to be construed so as to limit the present invention or otherwise to exclude any other such embodiments, adaptations, variations, modifications, and equivalent arrangements. The claimed invention is limited only by the following claims.

What is claimed is:

1. An applicator for applying a barbed fastener to a body tissue, the applicator comprising:
    an elongated tubular portion having a longitudinal axis extending from a proximal end to a distal end and having a tube interior accessible by proximal and distal tube openings, the tube interior being sized and configured for receiving the barbed fastener;
    an indexer disposed at least partially inside the tube interior, the indexer having an elongated indexer body member and a fastener engaging portion adapted to engage the barbed fastener and move the barbed fastener from an initial fastener position in the tube interior to a firing position as the indexer moves from a first longitudinal position to a second, more distal longitudinal position;
    a driver disposed at least partially inside the tube interior, the driver having a driver engaging portion at its distal end, the driver engaging portion being adapted to engage the barbed fastener in the firing position and selectively apply an ejection force to the barbed fastener, thereby ejecting the barbed fastener from the tube interior through the distal opening; and
    a driver actuator assembly adjacent the driver at its proximal end, the driver actuator assembly being adapted for selectively imparting an impulse force to the driver,
    wherein the driver is configured for transmitting the impulse force to the barbed fastener and the ejection force is the impulse force transmitted to the barbed fastener by the driver,
    wherein the barbed fastener comprises a head portion having a fastener passage formed therethrough and wherein the elongated indexer body member is configured for slidable disposition through the fastener passage.

2. The applicator of claim 1, wherein the ejection force is applied to the barbed fastener by the driver as the driver is moved distally from a pre-firing driver position to a distal-most driver position adjacent the distal tube opening.

3. The applicator of claim 2 wherein the applicator is configured for operation through a repeatable operation cycle comprising:
    an initial stage, in which the indexer is in its first longitudinal position and the driver is in its distal-most position;
    a pre-firing stage, in which the indexer is in its second, more distal longitudinal position and the driver is in its pre-firing position; and
    a post-firing stage, in which the indexer is in its second, more distal longitudinal position, and the driver is in its distal-most position.

4. The applicator of claim 3, wherein the indexer and driver are operably coupled with an actuation assembly configured to selectively control and coordinate movement of the indexer and driver from their initial stage positions to their pre-firing stage positions, from their pre-firing stage positions to their post-firing stage positions, and from their post-firing stage positions back to their initial stage positions.

5. The applicator of claim 4, wherein the actuation assembly comprises a trigger configured for rotational movement between an initial trigger position, a pre-firing trigger position and a post-firing trigger position, the trigger and actuation assembly being adapted so that movement of the trigger from the initial trigger position to the pre-firing trigger position causes the indexer and driver to move from their initial stage positions to their pre-firing stage positions, further movement of the trigger to the post-firing trigger position causes the indexer and driver to move from their pre-firing stage positions to their post-firing stage positions, and movement of the trigger back to the initial trigger position causes the indexer and driver to move from their post-firing stage positions back to their initial stage positions.

6. The applicator of claim 1, wherein:
    the tube interior is sized and configured for receiving one or more additional fasteners substantially identical to the barbed fastener, the additional fasteners being serially positionable within the tube interior proximal to the barbed fastener along the longitudinal axis,
    the indexer has one or more additional engaging portions adapted to engage the additional fasteners and to move each of the additional fasteners from a first longitudinal fastener position to a second more distal longitudinal fastener position at the same time the indexer moves the barbed fastener from its initial fastener position to its firing position.

7. The applicator of claim 6, wherein the second longitudinal position of the distal-most of the additional fasteners is the same as the initial fastener position of the barbed fastener.

8. The applicator of claim 6 further comprising: means for preventing the additional fasteners from moving in a proximal direction when the indexer returns from its second, more distal longitudinal position to the first longitudinal position.

9. The applicator of claim 6, wherein the elongated tube portion comprises one or more lance tabs projecting inward from an inner surface of the elongated tube portion at an angle toward the distal end of the elongated tube portion and capable of flexing outward, the lance tabs being configured to engage and prevent the proximal movement of the additional fasteners while allowing their distal movement by the indexer.

10. The applicator of claim 1 wherein the driver actuator assembly comprises:

a slideable plunger configured and positioned to engage the distal end of the driver and to slideably move between a proximal position and a distal position, said movement between the proximal position and the distal position being usable to impart the impulse force to the driver.

11. The applicator of claim 10 wherein the driver actuator assembly further comprises:

a biasing spring configured to bias the slideable plunger in a distal direction, wherein the slideable plunger is operatively coupled to a trigger configured to selectively detain the slideable plunger in the proximal position and to selectively release the slideable plunger, thereby allowing the slideable plunger to move from the proximal position to the distal position due to the bias of the biasing spring.

* * * * *